United States Patent [19]

McPhee

[11] 4,406,042
[45] Sep. 27, 1983

[54] TUBING CLIP

[75] Inventor: Charles J. McPhee, Huntington Beach, Calif.

[73] Assignee: American Hospital Supply Corporation, Evanston, Ill.

[21] Appl. No.: 253,343

[22] Filed: Apr. 13, 1981

[51] Int. Cl.³ .............................................. F16G 11/00
[52] U.S. Cl. ................................... 24/130; 24/129 A
[58] Field of Search ................ 24/130, 129 A, 129 B, 24/129 D, 336; 251/4, 6, 7

[56] References Cited

U.S. PATENT DOCUMENTS

| 479,509 | 7/1892 | Heaphy, Jr. | 24/129 A |
| 2,810,172 | 10/1957 | Wiglesworth | 24/130 |

Primary Examiner—Jay N. Eskovitz
Attorney, Agent, or Firm—Mary Jo Kanady

[57] ABSTRACT

A tubing clip is disclosed herein which comprises a body member forming a pair of channels through which a flexible tube may be passed, each of which is provided with a means for narrowing said channel at one end which narrows the channel sufficiently to prevent the tubing from slipping through the channels unaided while permitting the flow passage of the tube to remain open.

9 Claims, 6 Drawing Figures

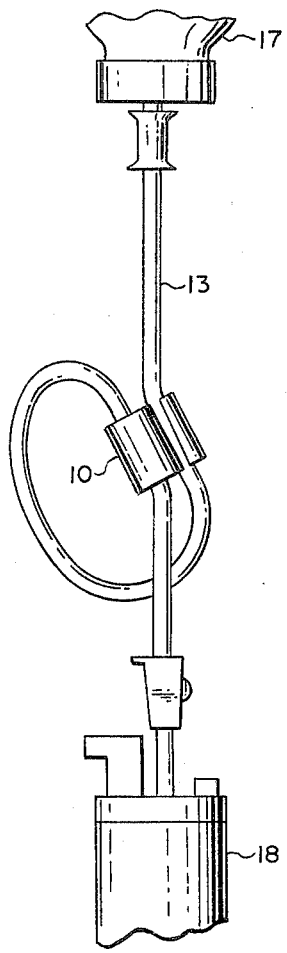
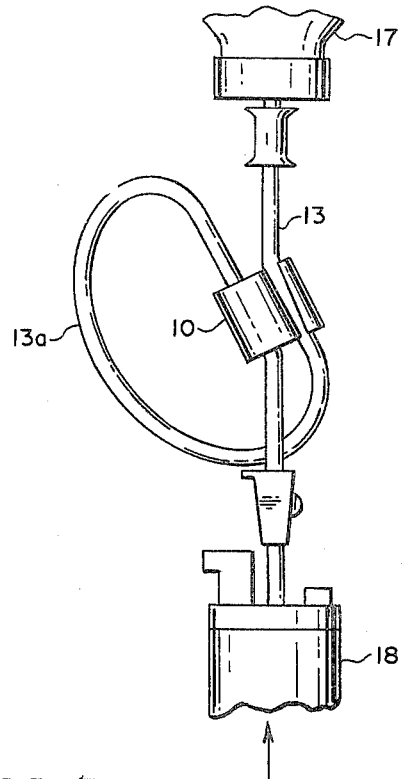
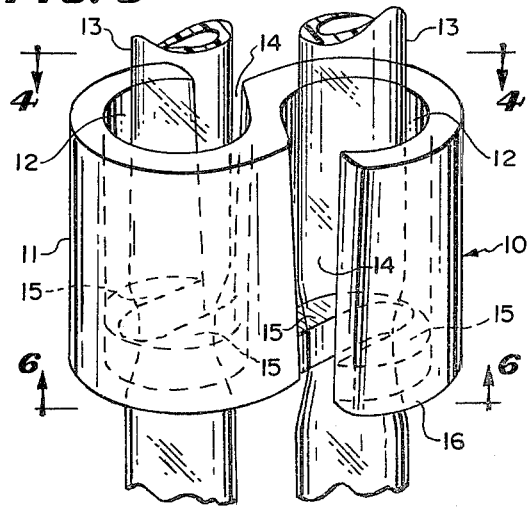
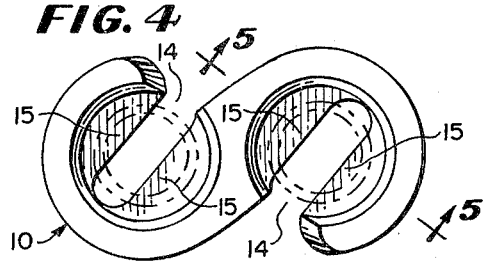
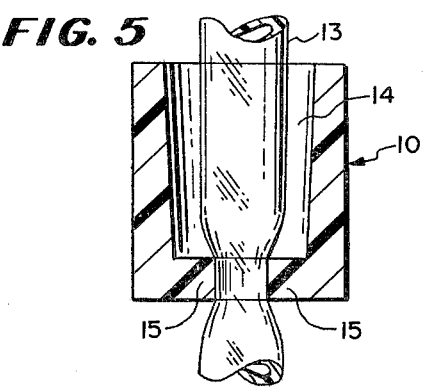
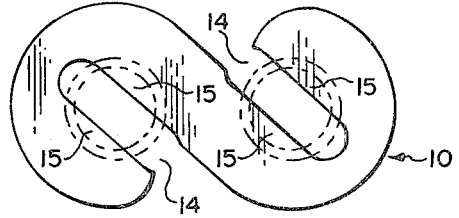

TUBING CLIP

BACKGROUND OF THE INVENTION

When filling an intravenous (I.V.) administration set such as the METRISET which is used for continuous or measured volume administration from a container of the solution being administered, the fill time can be decreased by using a longer length of tubing between the solution container and the measured voluem chamber. The longer tubing permits more head to build, thus increasing the flow. A problem occurs when the longer tubing is used, however, because the administration set then hangs too low. The present invention solves that problem by providing a tubing clip comprising a body member having a pair of channels through which a flexible tube can be passed, each channel being provided with a means for narrowing said channel at one end which narrows the channel sufficiently to prevent the tubing from slipping through the channel unaided while permitting the flow passage of the tube to remain open. By changing the size of the loop, medical personnel can raise or lower the measured volume chamber as needed. In addition to allowing faster fill times, the tubing clip allows the administration set to be easily adjusted to the eye-level of medical personnel of varying stature without changing the height of the intravenous solution container. Furthermore, the loop makes it easy to hang the administration set out of the way when the solution container is being changed.

Although a tubing clip is presently available in this field which comprises an S-shaped body member having a pair of channels through which a flexible tube may be passed, this clip only functions to hold two pieces of tubing in close proximity. It does not have a means for narrowing the channel at one end of each channel as does the tubing clip of the present invention. Therefore, it does not grasp the tubing as securely as the clip of the present invention. In addition, it cannot control the portion of the tubing which will slide through the clip as does one embodiment of the present invention and, therefore, does not facilitate the raising and lowering of an I.V. administration set as does the clip of the present invention.

SUMMARY OF THE INVENTION

The present invention provides a tubing clip for securing a loop of flexible tubing, said clip comprising a body member forming a pair of channels through which the flexible tubing can be passed, and a means for narrowing said channels formed at one end of each of said channels, the opening through said narrowing means narrowing the channel sufficiently to prevent the tubing from slipping through the channel unaided while permitting the flow passage of the tubing to remain open.

An advantage of the present invention is that the narrowing means at one end of each channel of the tubing clip clasps the tubing firmly and prevents the tubing from slipping through the channels. This permits a longer tubing to be used between a volume measuring chamber of an I.V. administration set and the I.V. solution container, since the length of the tubing can be adjusted as desired by manually pulling the tubing through the tubing clip to raise the volume measuring chamber and by pulling on the volume measuring chamber to lower it. The clip will grasp the tubing firmly enough to prevent it from slipping through due to the weight of the I.V. administration set. Moreover, the use of longer tubing shortens the time needed to fill the administration set.

In a preferred embodiment of the present invention, the body member of the tubing clip has an S-shaped cross-section; however, it will be recognized that other configurations such as a body member having a cross-section in the shape of the number 3 are within the scope of the invention.

In another embodiment of the present invention, the means for narrowing said channels is a raised abutment.

In one embodiment of the present invention, the means for narrowing the channels narrows one channel of the tubing clip more than the other channel. Since the channel is narrower, the tubing passing through it is grasped more tightly and will not slide through that channel as readily as the tubing will slide through the other channel. Thus, making one channel narrower controls which portion of the tubing will slide through the clip. This facilitates raising and lowering the volume measuring chamber of an I.V. administration set attached to an I.V. solution container by flexible tubing which passes through the clip, since the more tightly clasped length of tubing will be maintained at the same length while the other length of tubing may be shortened or lengthened as needed to adjust the height of the administration set. In another embodiment of the present invention, a pair of longitudinal openings are formed in the body member which communicate respectively with said pair of channels for permitting the flexible tubing to be inserted in said channels through said openings.

In another embodiment of the present invention, the side opening through which the tubing is placed in the channels of the clip is wider at the end of the channel opposite the means for narrowing the channels and becomes narrower toward the end of the channel having the means for narrowing the channels. This wider opening at the end of the channel opposite the means for narrowing the channels makes it easier to insert and remove the tubing from the clip.

Therefore, it is an object of this invention to provide a clip which may be easily installed and retained on flexible tubing and which will permit the length of the tubing to be adjusted without removing the tubing clip.

It is another object of this invention to provide a tubing clip which will clasp the tubing tightly enough to prevent slipping but not so tightly as to cut off or appreciably restrict the flow through the tube.

It is a furthe object of this invention to provide a tubing clip of a simple, single-piece design which is dependable and inexpensive to manufacture.

Other features of the structure and its operation, and additional advantages and objects of the invention, will become apparent from the specifications and drawings.

THE DRAWINGS

FIG. 1 is a side view of a tubing clip, constructed in accordance with an embodiment of the present invention, holding a length of tubing which connects an I.V. solution container to the volume measuring chamber of an I.V. administration set;

FIG. 2 is a view similar to FIG. 1 illustrating how the clip may be used to shorten the tubing length between the solution container and the volume measuring chamber of the administration set;

FIG. 3 is an enlarged perspective view of the tubing clip shown in FIGS. 1 and 2 illustrating how the tubing is clasped by the raised abutments on one end of the tubing channels;

FIG. 4 is a top sectional view of the tubing clip shown in FIG. 3 taken along line 4—4 thereof;

FIG. 5 is a side sectional view of one channel of the tubing clip shown in FIG. 4 taken along line 5—5 thereof; and FIG. 6 is a bottom sectional view of the tubing clip shown in /FIG. 4 taken along line 6—6 thereof.

DETAILED DESCRIPTION OF THE INVENTION

As best illustrated in FIG. 3, the tubing clip 10 comprises a body 11 which is S-shaped in cross-section, thereby forming two parallel cylindrical channels 12 into which a flexible tube 13 may be placed through the side openings 14. The side openings 14, through which the tubing 13 is placed in the channels 12, narrow slightly toward the bottom of the tubing clip as is best shown by FIG. 5. In addition, the bottom or end portion of the tube-holding channels 12 is narrowed by raised abutments 15 which are sized so as to frictionally engage the flexible tubing 13 and clasp it securely without cutting off the flow of liquid in the tubing. The bottom of the raised abutments 15 which clasp the tubing 13 is in the same plane as the bottom 16 of the tubing clip. This illustrated more clearly in FIGS. 5 and 6. Although raised abutments 15 are utilized in the preferred embodiment to frictionally engage flexible tubing 13, it should be understood that any means for narrowing channels 12 will satisfy the requirements of the present invention. For example, the inner diameter of channels 12 could be tapered toward one end thereof in order to frictionally engage the flexible tubing.

In FIGS. 1 and 2, the tubing clip 10 is being used to adjust the length of the tubing 13 connecting an intravenous solution bottle 17 to the measured volume chamber of an intravenous administration set 18. FIG. 2 shows how the clip may be used to shorten the distance between solution bottle 17 and the volume measuring chamber 18 by taking up tubing 13 into a larger loop 13a.

As will be readily apparent, the clip of this invention is susceptible to many uses, though the basic concept remains the same. In use, the clip 10 is positioned on a flexible tube 13 by introducing the tube into the side openings 14 and between the raised abutments 15, as shown in FIG. 3. The raised abutments 15 are sized to frictionally grip the tube 13 without appreciably diminishing the flow passage at that point. The holding friction should be sufficient to maintain the clip in place on the tube without any additional holding features, but should be loose enough so that the tubing may be freely moved through the clip to adjust its length. In one embodiment of the invention, the raised abutments 15 may be sized to narrow one of the channels 12 more than the other in order to control which portion of the tubing 13 will slide through the clip when adjusting the tubing length.

The clip can be made from any material having the required strength and rigidity. It may conveniently be made from plastics since they are easy to work with and are relatively inexpensive to manufacture.

What I claim is:

1. A tubing clip for securing a loop of flexible tubing, said clip comprising a body member forming a pair of substantially parallel channels, each of said channels extending the length of said tubing clip, through which the flexible tubing can be passed, and means for narrowing said channels formed at one end of each of sand channels, the opening through said narrowing means defining two substantially parallel sidewalls which narrow the channel sufficiently to prevent the tubing from slipping through the channel unaided while permitting the flow passage of the tubing to remain open and permitting said tubing to be manually slipped through said channel without binding.

2. A tubing clip according to claim 1 further comprising a pair of longitudinal openings formed in said body member which communicate respectively with said pair of channels for permitting said flexible tubing to be inserted in said channels through said openings.

3. A tubing clip according to claim 2 wherein the diameter of said channels is greater than the width of said longitudinal openings whereby said flexible tubing will be restrained within said channels after being inserted through said openings.

4. A tubing clip according to claim 3 wherein said longitudinal openings are wider at the end of said channels opposite said narrowing means to facilitate insertion of said flexible tubing in said openings.

5. A tubing clip according to claim 1 wherein said narrowing means are raised abutments.

6. A tubing clip according to claim 5 wherein said raised abutments are formed in their respective channels at the same end of the tubing clip.

7. A tubing clip according to claim 5 wherein one raised abutment narrows the channel in which it is formed more than the other raised abutment.

8. A tubing clip according to claim 1 wherein said body member is defined by an S-shaped cross-section which forms a pair of channels through which the flexible tubing can be passed.

9. A tubing clip according to claim 1 which is manufactured from plastic.

* * * * *